(12) United States Patent
Haynes, Sr.

(10) Patent No.: US 11,925,259 B2
(45) Date of Patent: Mar. 12, 2024

(54) NIGHTSTAND FOR CONTINUOUS POSITIVE AIRWAY PRESSURE (CPAP) DEVICE

(71) Applicant: Allan W. Haynes, Sr., Montclair, NJ (US)

(72) Inventor: Allan W. Haynes, Sr., Montclair, NJ (US)

( * ) Notice: Subject to any disclaimer, the term of this patent is extended or adjusted under 35 U.S.C. 154(b) by 294 days.

(21) Appl. No.: 17/552,090

(22) Filed: Dec. 15, 2021

(65) Prior Publication Data
US 2022/0192374 A1    Jun. 23, 2022

Related U.S. Application Data

(60) Provisional application No. 63/126,876, filed on Dec. 17, 2020.

(51) Int. Cl.
*A47B 79/00* (2006.01)
*A47B 88/40* (2017.01)
(Continued)

(52) U.S. Cl.
CPC .............. *A47B 79/00* (2013.01); *A47B 88/40* (2017.01); *A61M 16/0057* (2013.01);
(Continued)

(58) Field of Classification Search
CPC . A47B 79/00; A47B 2220/0058; A47B 67/04; A47B 2220/0094; A47B 46/00; A61M 2209/08; A61M 16/162; A61M 2209/045; A61M 2209/084; A61M 2209/10; A61M 16/0003
See application file for complete search history.

(56) References Cited

U.S. PATENT DOCUMENTS

| | | | | |
|---|---|---|---|---|
| 654,062 A | * | 7/1900 | Haddox | B65H 61/00 312/285 |
| 5,399,007 A | * | 3/1995 | Marconet | A61B 50/13 312/249.8 |

(Continued)

FOREIGN PATENT DOCUMENTS

| | | | |
|---|---|---|---|
| AU | 2013232848 A1 | * 10/2014 | ........ A61M 16/0003 |
| CN | 110433386 A | * 11/2019 | |

(Continued)

*Primary Examiner* — Hanh V Tran
(74) *Attorney, Agent, or Firm* — Michael J. Brown (57) ABSTRACT

A nightstand designed to support and contain various CPAP machines and associated CPAP equipment including air tubing, cleaning devices and distilled water storage. Separate drawers and compartments are provided to house the CPAP machine, CPAP cleaning device, and water supply containers. Various openings are designed to increase utility and convenience in the operation and storage of CPAP devices and associated equipment. A pump may be provided to transfer water from water supply containers to the CPAP machine reservoir. The CPAP nightstand is designed to be located at bedside and provides easy access to the CPAP machine and its ancillary devices while keeping all equipment in dedicated drawers. Each dedicated drawer provides openings to allow passage of air tubing, water hoses and power cords. The CPAP nightstand also has generic drawers for additional storage.

11 Claims, 5 Drawing Sheets

(51) Int. Cl.
  *A61M 16/00* (2006.01)
  *A61M 16/06* (2006.01)
  *A61M 16/08* (2006.01)

(52) U.S. Cl.
  CPC ...... *A61M 16/021* (2017.08); *A61M 16/0666* (2013.01); *A61M 16/0875* (2013.01); *A47B 2220/0058* (2013.01); *A61M 2209/08* (2013.01)

(56) References Cited

U.S. PATENT DOCUMENTS

| | | | | |
|---|---|---|---|---|
| 5,611,553 | A * | 3/1997 | Schoeman | A47B 46/00 280/47.35 |
| 8,122,540 | B2 * | 2/2012 | Ardis | A47C 21/044 5/284 |
| 8,905,229 | B1 * | 12/2014 | Lane | A61M 16/06 206/349 |
| 9,060,599 | B1 * | 6/2015 | Jones | A47B 23/06 |
| 9,671,129 | B1 * | 6/2017 | Lu | F24H 3/0411 |
| 9,733,011 | B2 * | 8/2017 | Ferrari | A61M 1/062 |
| 2007/0045152 | A1 * | 3/2007 | Kwok | A61M 16/00 206/733 |
| 2011/0109211 | A1 * | 5/2011 | Kirkeby | A47B 88/90 312/223.6 |
| 2016/0106209 | A1 * | 4/2016 | Miller | A47B 79/00 312/209 |
| 2019/0344102 | A1 * | 11/2019 | Bradford | A61M 16/00 |
| 2020/0214459 | A1 * | 7/2020 | Venditto | A47C 19/22 |
| 2021/0138517 | A1 * | 5/2021 | Kakar | B08B 9/023 |

FOREIGN PATENT DOCUMENTS

| | | | | |
|---|---|---|---|---|
| CN | 209950722 | U * | 1/2020 | |
| DE | 202010016832 | U1 * | 5/2011 | ............ A47B 23/04 |
| JP | 2020078404 | A * | 5/2020 | |
| RU | 96737 | U1 * | 8/2010 | |

* cited by examiner

Figure 9

NIGHTSTAND FOR CONTINUOUS POSITIVE AIRWAY PRESSURE (CPAP) DEVICE

PRIORITY

This application claims domestic benefit from provisional application No. 63/126,876, filed Dec. 17, 2020, and incorporated by reference.

FIELD OF INVENTION

The invention is in the field of furniture, specifically furniture adapted for use with medical devices.

BACKGROUND

According to the National Center for Biotechnology Information 50 to 70 million people in the US suffer from some form of sleep disorder and an estimated additional 10 million people in the US remain undiagnosed. And, according to Sleep Advisor, approximately 25 million adults suffer specifically from obstructive sleep apnea and consequently millions of Americans either use Continuous Positive Airway Pressure (CPAP) machines or require some form or equipment to assist with their breathing in order to get a good night's sleep.

A CPAP machine supplies a continuous stream of pressurized air that travels through flexible tubing to a CPAP mask worn on a user's face. To prevent dryness in the mouth and throat, many CPAP machines include a reservoir of water to humidify the pressurized air. The water may be supplied by a separate hose.

CPAP machines also require regular cleaning, especially of the mask and tubing. CPAP cleaning devices allow users to place the mask and tubing in a chamber for cleaning.

An object of the present invention is to meet the demand where many Americans who suffer from sleep apnea and use a CPAP machine, there are many challenges and obstacles that still remain in getting a good night's sleep. Added to that are accessory devices, set up, care, storage and maintenance and you have a potential for a lot of clutter, anxiety, disorganization and spills that can easily contribute to an already challenging sleep situation. These are ongoing considerations for anyone using CPAP machines and their associated accessories. Most CPAP users place their CPAP device in the only logical and available space to them, which is atop their nightstand. Unfortunately, their nightstand is most likely a furniture piece they purchased at a typical furniture store and is not designed to address the needs of a CPAP user. Consequently, they lose space for typical bedside items in sacrifice to the CPAP machine. It is more than likely that their generic piece of furniture was not designed to address sanitary conditions, added clutter in addition to potential noise disruption. Much of the CPAP device, its accessories and components end up inconveniently on or around their existing nightstand increasing hazards like tripping, disorganization, anxiety and unsanitary conditions. Containers of water may end up on the floor near the nightstand causing potential tripping hazards at night when leaving the bed to use the bathroom or other nighttime activity. Wires and hoses or air tubing might be disorganized contributing to the general lack of a focused set up. Users may experience a lack of space on their nightstand for non-CPAP related materials like medications, reading materials, a glass of water, eyeglasses and other such material.

Problems arising from not having a dedicated support for a CPAP machine include:

(a) Water Spills—Chronic spills are a way of life for CPAP users because the CPAP machine must be filled with water before each use usually every night before bed, and spilling due to overflow or missing the water inlet leads to staining and damaging existing furniture.

(b) Tumbles—Pulling the CPAP machine off the nightstand because a user turns over during sleep is a constant hazard for CPAP users. As the CPAP machine merely sits on atop of most nightstands, the CPAP machine can easily tumble to the floor, causing nighttime disruption and spills. Additionally, the air tubing, water hose, and/or power cord can pull other interfering objects to the floor depending on whatever else is sitting on the nightstand.

(c) Noise—Although most modern CPAP devices are very quiet, some may make noise and some cleaning devices may make more noise during cleaning cycles. For some this may be a noisy distraction even if the user is in another room during operation. Having the CPAP device located in a configuration where it can remain indefinitely (i.e. in a drawer) reduces sound transmission even further and additionally contributes to bedtime tranquility.

(d) Storage—Using CPAP devices is relatively common for many Americans; however, many of those same people are ill equipped to support the running and use of these devices in their bedrooms. In other words, they have no safe and secure place to store, run and clean their devices particularly when safety and security is most needed—while they sleep. Most users simply store the device on top of their nightstand along with all the accessories and cleaning equipment. Additionally, water jugs filled with distilled water and other material might wind up on the floor causing tripping hazards at night.

SUMMARY

A nightstand for the storage of a CPAP device and associated equipment is provided, allowing for drawers and compartments to store the CPAP device and associated equipment, while providing openings for the passage of air tubing, water hoses, and power cords. Specific drawers are provided for the CPAP device and the CPAP cleaning device to facilitate their operation. The nightstand also provides storage for water supplies, and provides a pump to transfer water from a water supply to a reservoir in the CPAP device.

Because all CPAP and accessory devices are located in drawers, the sound generated by the equipment is dampened during operation. Since each device is located within a drawer, the devices are secure and no risk of tumbling to the floor is present. Clutter is no longer an issue with the CPAP nightstand because all devices are stored safely in specific drawers. The CPAP nightstand can provide the user with a measure of organization, because all CPAP and related equipment have been organized into well thought out, hand crafted locations. And finally the user may experience less anxiety as now there is space for more routine nighttime items including a top surface for the nightstand that is completely free of CPAP equipment.

The CPAP nightstand is conveniently located at the bedside and can be configured for placement at either the right or left side of the bed for optimum functionality and convenience. The CPAP machine, cleaning device, distilled water containers and automatic reservoir fill are all carefully designed and placed in an integrated solution that helps to make the use and cleaning of the CPAP equipment an uneventful and worry-free experience. Less worry and anxiety help to encourage a more tranquil environment and a peaceful night's sleep.

The CPAP nightstand is a fully integrated solution for anyone who uses CPAP devices on a regular or semi-regular basis. Each component of the CPAP device and accessory devices have been carefully considered in a design that places each item in a special location to provide both security and functionality. The CPAP nightstand is a piece of furniture constructed of natural wood materials, handcrafted and finished to last generations.

DETAILED DESCRIPTION

The nightstand (100) is preferably of a similar size as conventional bedside nightstands, but is adapted to house a CPAP machine and related equipment. The top surface (1) of the nightstand (100) is preferably a typical height above the floor as conventional nightstands. Nightstand (100) has an access side panel (7) and a rear panel (15).

Access side panel (7) includes access door (4) and access port (13). Access side panel (7) preferably includes switch (50). Air tubing (27) from the CPAP device (200) extends from within upper drawer (5) through access port (13) and a CPAP mask would be attached to a free end of air tubing (27) for use.

Rear panel (15) has at least one opening (30) to allow for power cords, hoses, and tubing to pass therethrough. Preferably, one opening (30) is used for power cords, but additional openings (3) may be used for hoses or tubing to accommodate different types of CPAP machines and associated equipment.

On one side of nightstand (100) are two drawers, an upper drawer (5) and a lower drawer (9), preferably vertically stacked and located on the side of nightstand (100) that would be closest to the bedside. In the drawings, upper drawer (5) and lower drawer (9) are shown on the left side of nightstand (100), but the orientation of nightstand (100) may be reversed for use on another side of a bed.

The upper drawer (5) preferably houses a CPAP device (200) and the lower drawer (9) preferably houses a CPAP cleaning device (300). The upper drawer (5) is preferably located at a sufficient distance above the floor so that it may be easily reachable by a user from various positions on the bed, including laying down or sitting. The upper drawer (5) preferably provides a clear interior space to accommodate most CPAP machines on the market today. One side of the upper drawer (5) has a cut-out (40) that lines up with access door (4). The drawer cut-out (40) provides for convenient operation of the CPAP device (200) through access door (4).

Access door (4) allows the user access to adjust the settings of the CPAP device (200), including turning the machine on or off, and to view the water level of the CPAP device (200) within nightstand (100) without having to open the upper drawer (5) and/or move the CPAP device (200). Preferably, upper drawer (5) uses undermount drawer slides in lieu of typical side mount drawer slides that would otherwise interfere with the access door (4).

The upper drawer (5) has numerous specific design implementations that address the CPAP device usage and functionality and optimize it for the user experience. There are ports (3) in the rear of the upper drawer (5) to accommodate the air tubing (27), the power cord (26) and water hoses (18) of the CPAP device (200).

The air tubing (27) for CPAP device is typically flexible corrugated plastic. Nightstand (100) provides at least one fastener to secure the air tubing adjacent to the side panel access port (13). Securing air tubing (27) allows the air tubing to move freely outside of the nightstand (100) while remaining stable within the nightstand (100), allowing the drawer to move without destabilizing the CPAP device, as well as allowing the user to move with the CPAP mask without moving the CPAP device.

Lower drawer (9) is preferably below upper drawer (5) and provides space for housing a CPAP cleaning device (300). Rear panel (91) at the rear of lower drawer (9) allows for the CPAP device power cord to pass therethrough. The interior dimensions of lower drawer (9) allow for the accommodation of various common CPAP cleaning devices. Notch (6) in the front of lower drawer (9) allows for CPAP air tubing (27) to pass therethrough while the lower drawer (9) is in the closed position. This allows the CPAP mask with the attached air tubing (27) to be placed in the CPAP cleaning device (300) during cleaning. The nightstand (100) allows for cleaning the CPAP mask, tubing and CPAP machine while all components are still connected, thereby making routine maintenance efficient and less time-consuming.

Preferably adjacent to the lower drawer (9) is a compartment (10) which can store water containers (23) used for filling the reservoir of the CPAP device (200). Compartment (10) may be a drawer or open space with a door. Compartment (10) allows for water containers (23) to be placed adjacent to the lower drawer (9). In a narrow configuration of nightstand (100), compartment (10) may be located below lower drawer (9). Opening (28) through vertical separator panel (8) and/or opening (16) of horizontal panel (11) of the nightstand (100) provides an access path for hose (18) to travel between water containers (23) and the CPAP device (200), as well as opening (3) at the rear of the upper drawer (5). Compartment (10) preferably can hold at least four typical one gallon containers of distilled water.

Figure 1:
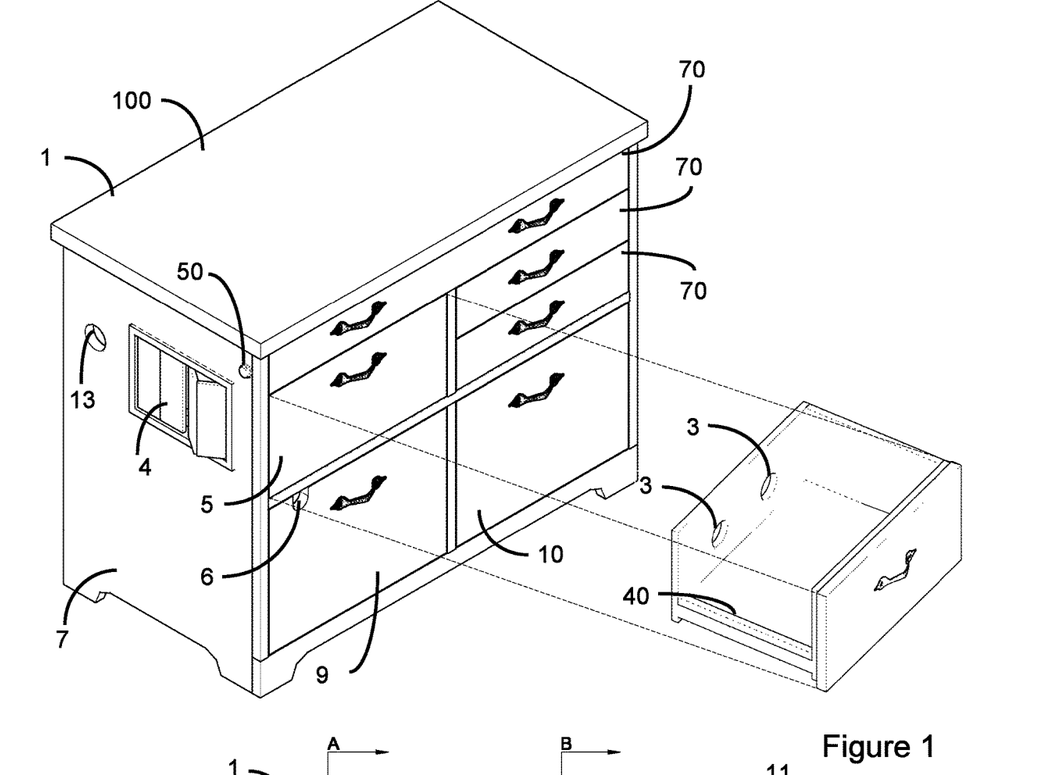
FIG. 1 is a top perspective of a preferred embodiment of the CPAP Nightstand unit and the CPAP drawer shown in an exploded view.
Figure 2:
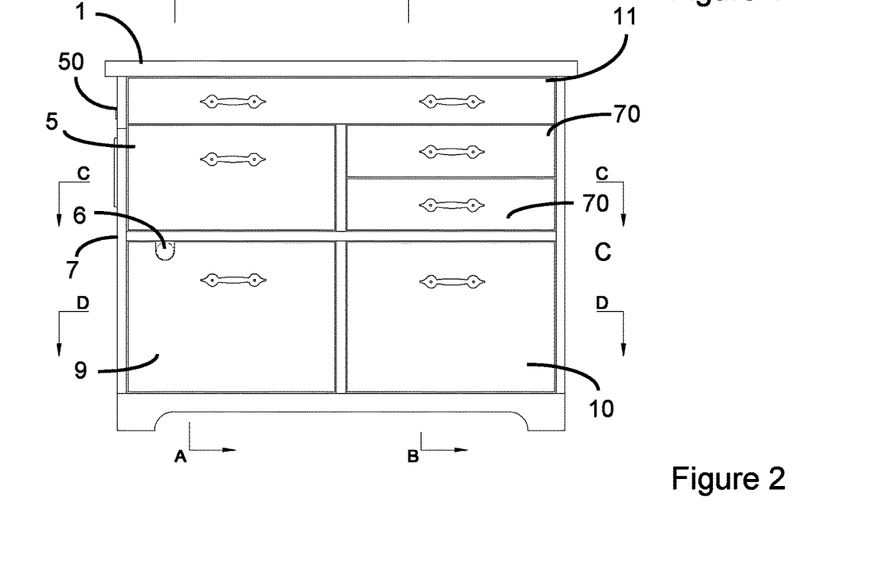
FIG. 2 is a front elevation thereof, showing each drawer front, the base and the top profiles.
Figure 3:
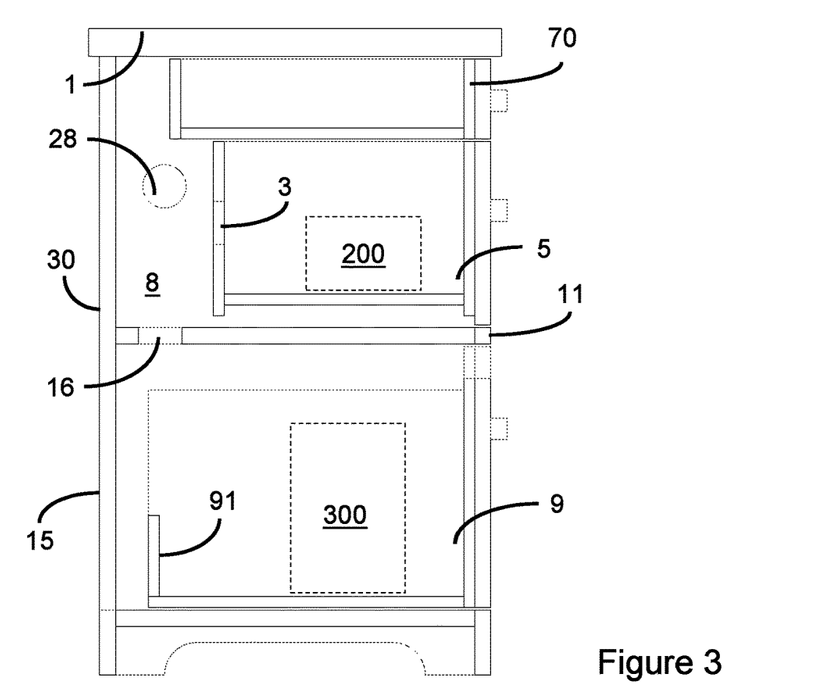
FIG. 3 is a cross-sectional view along line A-A of FIG. 2.

FIG. 3 shows section A-A through the left side of the unit, showing rear panel (15) of the nightstand (100) equipped with a port (30) for accommodating power cords. Section A-A also shows an opening (16) in the horizontal middle panel (11) of nightstand (100) allowing for the passage of power cords and hose connections for water.

Figure 4:
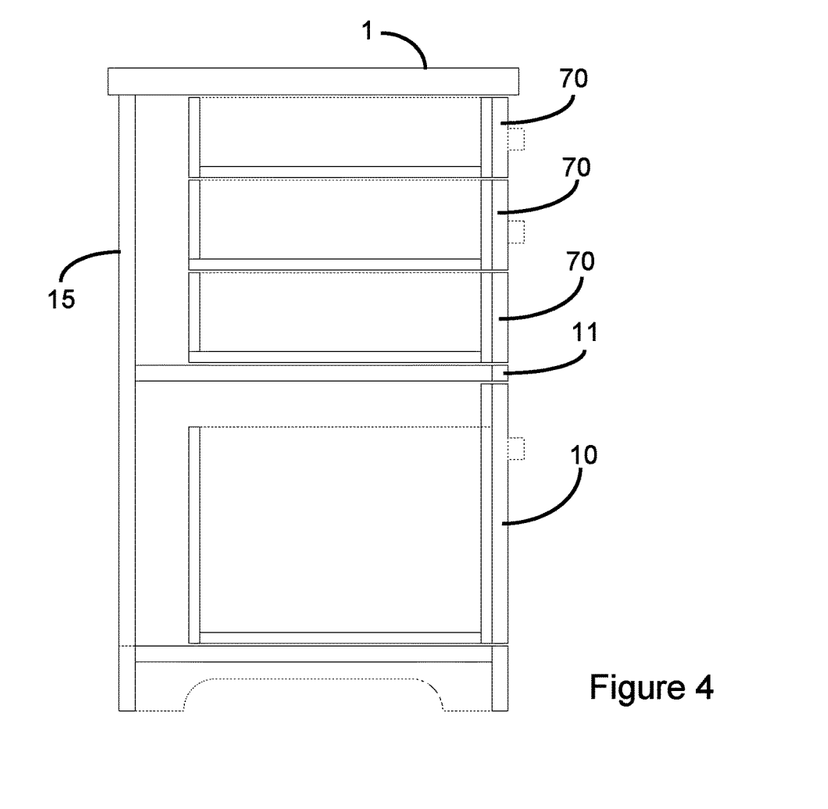
FIG. 4 is a cross-sectional view along line B-B of FIG. 2.

FIG. 4 shows section B-B shows the profiles of the compartment (10) and a generic storage drawer (70).

The water hoses (18) for providing water from water containers (23) in compartment (10) to the CPAP device (200) are preferably fixed to the inside of the rear panel (15). Preferably the water hose (18) is a flexible hose that allows for extension and contraction, thereby permitting the upper drawer (5) to be opened and closed without pulling on or displacing the CPAP device within upper drawer (5).

Figure 5:
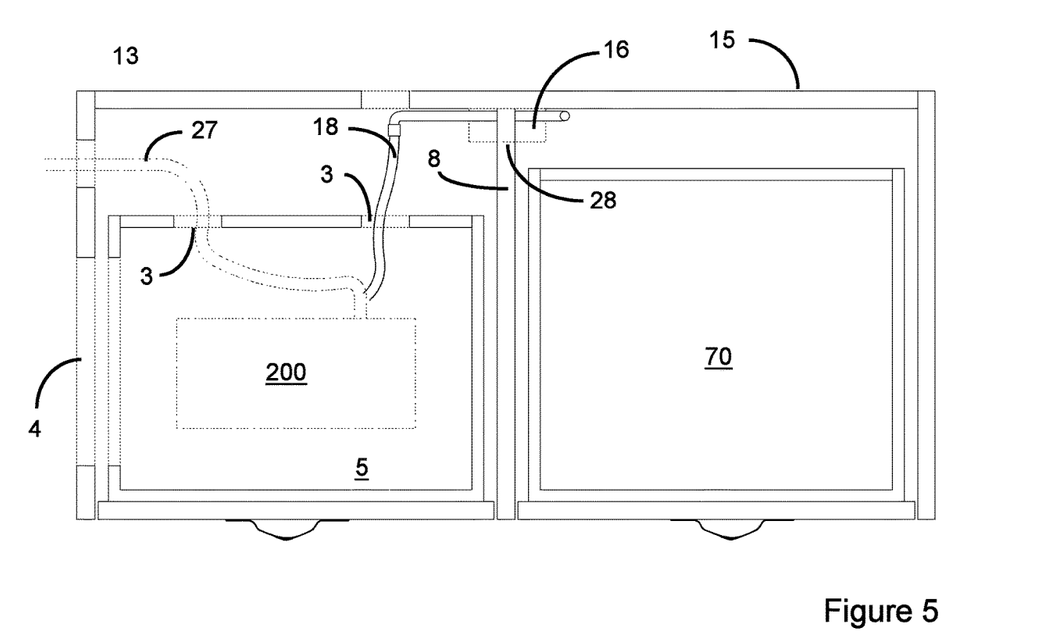
FIG. 5 is a cross-sectional view along line C-C of FIG. 2.

FIG. 5 (Section C-C) is a view from above looking at the upper drawer (5) and a generic storage drawer (70). The ports (3) on the rear panel of upper drawer (5) accommodate power cords, water hose (18), and air tubing (27). The opening (16) through the horizontal middle panel (11) allows for power cords and water hose to access the CPAP device and the rear panel port (30) for connection to an electrical outlet. The opening (28) through the vertical panel (8) serves a similar purpose as opening (24). The rear panel port (30) is preferably located to minimize distances so that all devices that require power have a relatively short run for their respective power cords to reach an outlet.

Figure 6:
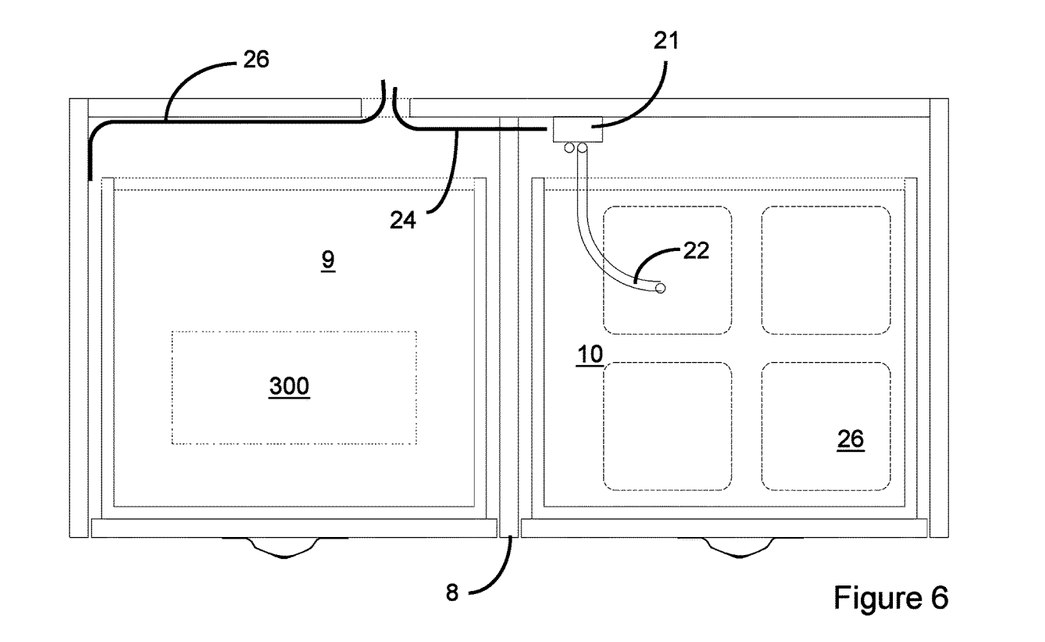
FIG. 6 is a cross-sectional view along line D-D of FIG. 2.
Figure 7:
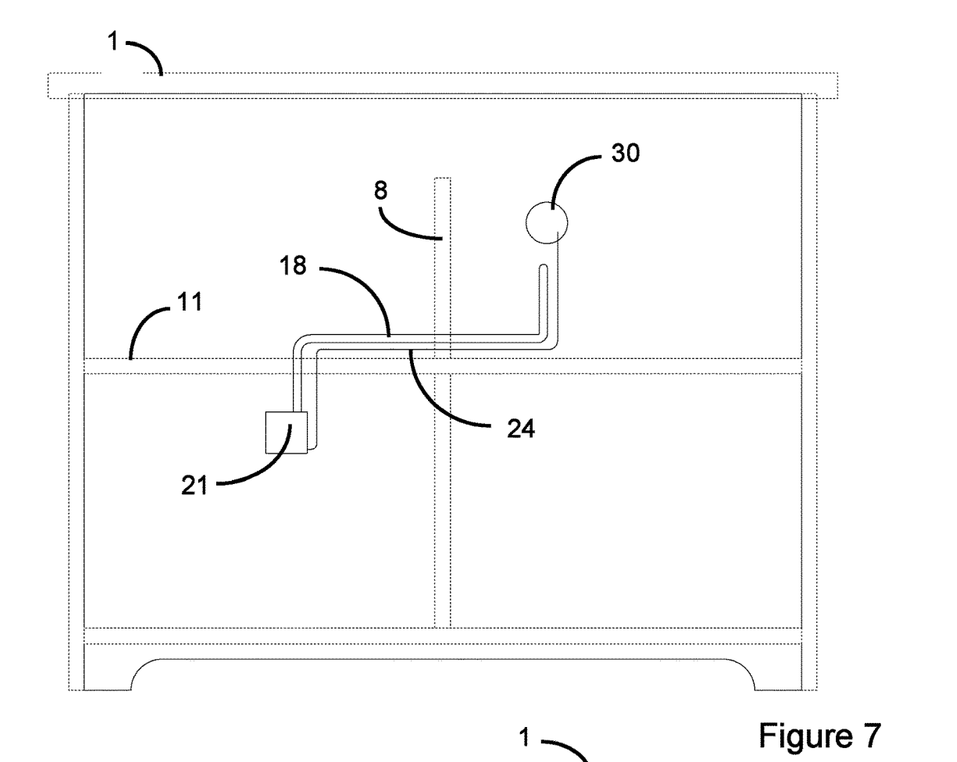
FIG. 7 is a rear view showing internal features.
Figure 8:
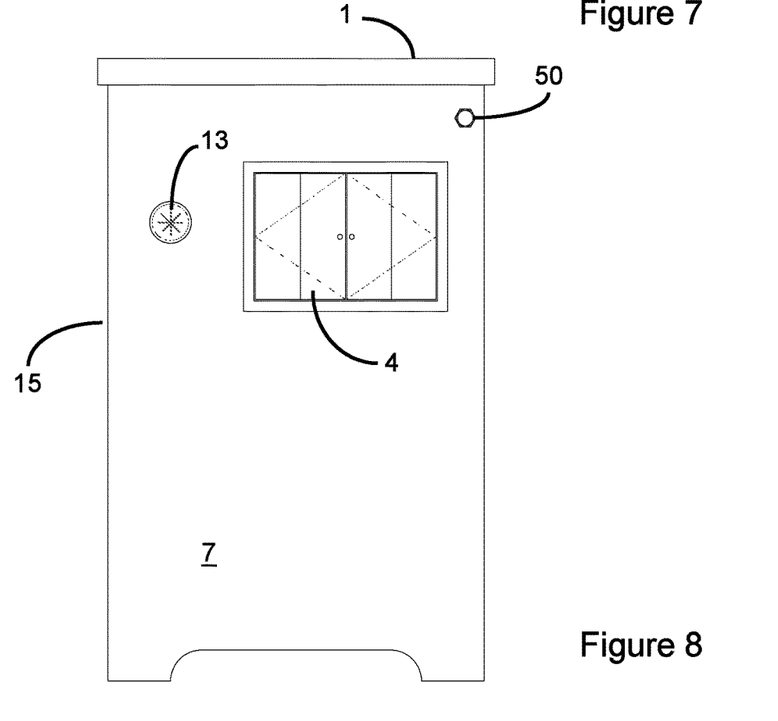
FIG. 8 is a left side view, showing the access door.
Figure 9:
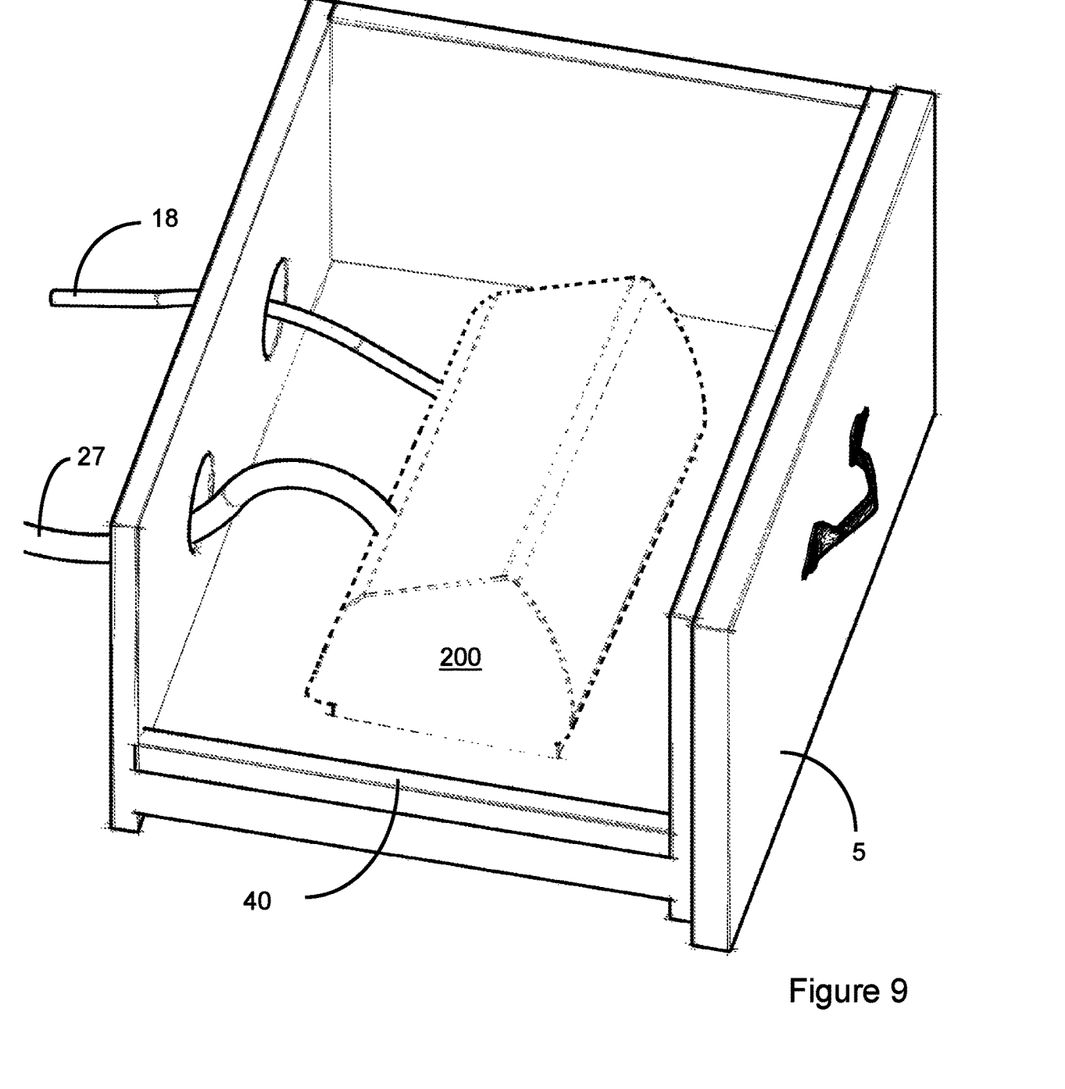
FIG. 9 is a perspective view of the upper drawer of the nightstand, showing the placement of a CPAP machine and its associated air tubing and water hose.

FIG. 6 shows an automatic water fill feature to deliver water from distilled water containers in compartment (10) directly into the reservoir or tub of a CPAP device, and can save users the effort of continually having to get out of bed to fill the tub of the CPAP machine after they have settled into bed.

This feature is comprised of a water pump (21) which may be mounted to the rear panel (15) of the nightstand (100). Water pump (21) is preferably mounted in such a way that allows compartment (10) to be operated or removed without interfering with the pump's wiring. The intake hose (18) is routed to a distilled water container in compartment (10) and the supply hose is routed through ports (16 & 28) in the horizontal interior panel (11) and vertical interior panel (8) and connects directly to the reservoir of the CPAP machine. The pump power cord (24) is run through a port (3) at the rear of the upper drawer (5), which is provided access to the main power port (30) located on the rear panel (15) of the nightstand (100).

The pump (21) may be controlled by switch (50). Switch (50) is preferably a push button and is located on the side panel (7) adjacent to the bed for convenient access. Switch (50) is preferably located near top surface (1) and may provide momentary power to the pump (21) allowing water to be pumped from the source and into the reservoir of the CPAP machine while the switch (50) is pressed. Upon release of switch (50) power is cut off and the pump (21) shuts off thereby reducing or eliminating the risk of excess water being delivered to the reservoir or the upper drawer (5). The location of switch (50) is designed to not interfere with the operation of the drawer and be conveniently located to reach from the bedside.

The drawers and compartments of the nightstand unit (100) are preferably outfitted with cable and hose retention clips to allow the drawers and/or doors to be opened and closed without overextending the power cords, water hoses or air tubing.

The access door (4) on the side panel (7) of the nightstand (100) serves to provide convenient access to the CPAP device. It is easily accessible from the bedside and is sized to have minimal impact when opening the doors while allowing a hand and arm to reach in to manage the device's functions. The doors are preferably hinged and may be secured with magnetic catches.

The nightstand (100) is preferably 11 cubic feet and has at least three specific drawers and/or compartments that are specially designed for CPAP devices and accessories. Each of these drawers is also optimally positioned for efficient functionality and convenient use. Additional drawers (70) can be provided for general use by a user.

Sanitary conditions are addressed where all interior and exterior surfaces are coated with a marine grade epoxy resin that is highly resistant to water. The nightstand (100 may be finished with a durable clear coat of wood finish that protects against water stains and is easily cleaned.

The CPAP Nightstand invention is preferably handcrafted from select natural woods to create a piece of furniture where all CPAP equipment, ancillary components and accessories are secured in specific drawer locations within the nightstand.

While certain novel features of the present invention have been shown and described, it will be understood that various omissions, substitutions and changes in the forms and details of the device illustrated and in its operation can be made by those skilled in the art without departing from the spirit of the invention.

I claim:

1. A nightstand for use with a Continuous Positive Airway Pressure (CPAP) machine, the CPAP machine comprising a base unit with water reservoir, a mask, a water supply hose, and air tubing connecting the base unit to the mask, the nightstand comprising:
   a furniture body with a front side, a top surface, a first side panel, an opposite side panel, and rear panel, where the front side comprises a plurality of openings capable of holding drawers, and where the first side panel and opposite side panels are on opposite sides of the furniture body;
   a first drawer capable of sliding in and out of the front side of the furniture body, the first drawer having a first drawer bottom panel, a first drawer front panel, a first drawer rear panel, a first drawer full side panel and a first drawer partial side panel, where the first drawer full side panel and first drawer partial side panel are on opposite sides of the first drawer bottom panel, and the first drawer partial side panel is adjacent to the first side panel of the furniture body;
   a second drawer capable of sliding in and out of the front side of the furniture body, the second drawer having a second drawer bottom panel, a second drawer front panel, a second drawer rear panel, a second drawer right side panel and a second drawer left side panel, where the second drawer front panel comprises a second drawer front opening;
   a side door in the first side panel of the furniture body configured to allow easy access to the CPAP machine;
   a first access port in the first side panel of the furniture body, the first access port capable of allowing the air tubing to pass therethrough;
   where the first drawer is capable of holding the base unit of the CPAP machine, and where the second drawer is capable of holding a CPAP cleaning device.

2. The nightstand of claim 1, further comprising:
   a drawer access port in the first drawer rear panel, the drawer access port capable of allowing at least one of the air tubing and water hose to pass therethrough.

3. The nightstand of claim 1, further comprising:
   a compartment capable of holding a water supply container.

4. The nightstand of claim 3, further comprising:
   an access path allowing the water hose from the CPAP machine to contact the water supply container.

5. The nightstand of claim 3, further comprising:
   a pump connected to the water supply container by a supply hose.

6. The nightstand of claim 5, further comprising:
   an access path allowing the water hose from the CPAP machine to contact the pump.

7. The nightstand of claim 5, further comprising:
   a switch electrically connected to the pump, the switch located on the first side panel.

8. The nightstand of claim 1, further comprising a generic drawer.

9. The nightstand of claim 1, further comprising power connections for the CPAP machine and CPAP cleaning device.

10. The nightstand of claim 3, where the compartment is located to a side of the second drawer, opposite the first side panel of the nightstand.

11. The nightstand of claim 3, further comprising:
- a horizontal panel between the upper drawer and the lower drawer, the horizontal panel comprising a horizontal opening;
- a vertical panel between the lower drawer and the compartment, the vertical panel comprising a vertical opening; and
- a second access path allowing the water hose from the CPAP machine to contact the water supply container, the second access path including at least one of the horizontal opening and the vertical opening.

* * * * *